Figure 1:
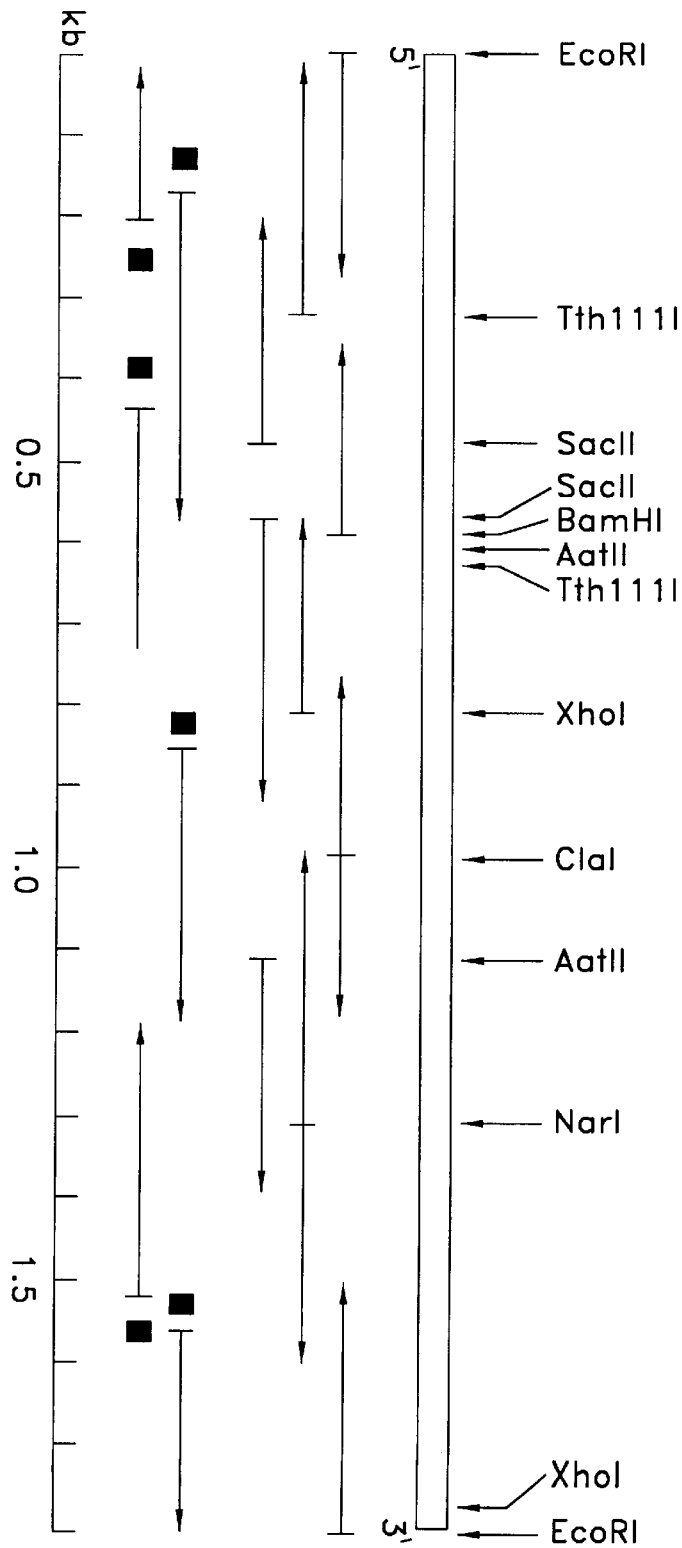

United States Patent [19]

Saavedra-Duran et al.

[11] Patent Number: 6,077,690

[45] Date of Patent: Jun. 20, 2000

[54] **CLONING AND EXPRESSION OF A PROTEIN ANTIGEN OF *TOXOPLASMA GONDII***

[76] Inventors: Rafael Saavedra-Duran, Galeana, 314 Centro, Cuernavaca, Mor. 62000, Mexico; Pascal Herion, Copilco, 300 EdiF7 #204 Colonia Copilco - Universidada cp, 04360 Mexico, D.F., Mexico

[21] Appl. No.: 08/458,922

[22] Filed: Jun. 2, 1995

Related U.S. Application Data

[63] Continuation of application No. 08/075,571, filed as application No. PCT/EP91/02423, Dec. 16, 1991, abandoned.

[30] Foreign Application Priority Data

Dec. 20, 1990 [GB] United Kingdom .................. 9027728

[51] Int. Cl.$^7$ .............................. C12P 21/06; C12N 1/20; C12N 15/00; C07H 21/04
[52] U.S. Cl. .................. 435/69.3; 435/252.3; 435/320.1; 435/325; 530/350; 536/23.7
[58] Field of Search ................................. 435/69.3, 252.3, 435/320.1, 325; 530/350; 536/23.7

[56] References Cited

U.S. PATENT DOCUMENTS 4,877,726  10/1989  Suzuki et al. .
4,879,213  11/1989  Fox et al. .

FOREIGN PATENT DOCUMENTS 0301961  2/1989  European Pat. Off. .

OTHER PUBLICATIONS

R. Saveedre et al., "Human T cell clone identifies a potentially protective 54–kDa protein antigen of *Toxoplasma gondii* cloned and expressed in *Escherichia coli*", *Journal of Immunology*, vol. 147, No. 6, (Sep. 1991).

Prince et al., "Cloning of cDNAs encoding a 28 kilodalton antigen of *Toxoplasma gondii*", *Molecular and Biochemical Parasitology*, 34, 3–14 (1989).

R. Sveedra et al., "Monoclonal antibodies identify new *Toxoplasma gondii* soluble antigens", *Hybridoma*, vol. 5, No. 5, pp. 453–463 (Oct. 1990).

Burg et al., "Molecular Analusis of the Gene Encoding the Major Surface Antigen of *Toxoplasma gongii*", *The Journal of Immunology*, vol. 141, No. 10, 1988, pp. 3584–3591.

Burgess et al., "Possible Dissociation of the Heparin–Binding and Nitrogen Actimates of Heparin–Binding Growth Factor from its Receptor–Binding Activities by Sets–Diasted Mytogensis of a Single Lysine Residues", *The Journal of Cell Biology*, vol. 111, 1990, pp. 2129–2138.

Lazar et al., "Transforming Growth Factor Mutation of Adaptive Acid 47 and Lusins 48 Result in Different Biological Activities", *Molecular and Cell Biology*, vol. 8, No. 1, 1988, pp. 1247–1252.

Bowie et al., "Deciphering the Message in Protein Sequence: Tolerance to Amino Acid Substitution," *Science*, vol. 247, pp. 1306–1310.

Sallgaller et al. Cancer Immunol. Immuno. 39:105–116, 1994.

*Primary Examiner*—Anthony C. Caputa
*Assistant Examiner*—Mark Navarro

[57] ABSTRACT

An isolated DNA molecule encoding a protein comprising all or a portion of a 54 kDa protein of *Toxoplasma gondii* is disclosed. The protein is capable of reacting with antibodies present in the sera or other biological samples of humans or animals infected with *T. gondii*. A vector comprising the DNA molecule, a host cell transformed with the vector, and a method for recombinantly producing the protein are disclosed.

18 Claims, 3 Drawing Sheets

```
  1 GAATTCGGGGAAAACTGTGCGTCGGTCAGATCATCGTCGTGTCTTATCTGGCTAGCTGCC
      E  N  C  A  S  V  R  S  S  S  C  L  I  W  L  A  A

61 GCATTCTTTGTTTCGGCACTTGGCCACGTACAGCAAGGCGCTGGCGTTGTGCGGCCTCGC
      A  F  F  V  S  A  L  G ▽ H  V  Q  Q  G  A  G  V  V  R  P  R

121 CACTGGCAGAACTCGGAAGCCGCTGTTAGTGTCCGGCCGCCGGGAGGCGCGTCCCCTAGA
      H  W  Q  N  S  E  A  A  V  S  V  R  P  P  G  G  A  S  P  R

181 CATTTCCACAGCCCAATTGAGCCAGTAGCATTTATTGATGGGGAGCACGTTGAAGACAAG
      H  F  H  S  P  I  E  P  V  A  F  I  D  G  E  H  V  E  D  K

241 CATGGAGGCTCATGGCTGGAGCAGGAAGCGGCCGAGGAAGTGACCCCCTTACTGAACAGC
      H  G  G  S  W  L  E  Q  E  A  A  E  E  V  T  P  L  L  N  S

301 CACACAGAGACCCCGACACAGTCCCCCAGTGCTTTTAGAAGGTTACTCAGGCGTTTGCGT
      H  T  E  T  P  T  Q  S  P  S  A  F  R  R  L  L  R  R  L  R

361 TTTTGGCGACGTGGGAGGACAGGCGGATCAGATGGCGGAGGAGAACCACCGCAGACGCCT
      F  W  R  R  G  R  T  G  G  S  D  G  G  E  P  P  Q  T  P

421 CGCCCTTCCCTACCGACCCGACTGTTTCAGCATTTGCGGCGTGCGGCAGCAGCAATTCCC
      R  P  S  L  P  T  R  L  F  Q  H  L  R  R  A  A  A  I  P

481 GCGGCGGCATCTAGATTCTTTAGGAGATTTCGACGAGTCCAAGAACCTGTATTCCCTCCC
      A  A  A  S  R  F  F  R  R  F  R  R  V  Q  E  P  V  F  P  P

541 GACGAGTTTCCGGAGGATGTCGACACGAACCCTATGTATTTCCGCGGTACGGATCCTGGA
      D  E  F  P  E  D  V  D  T  N  P  M  Y  F  R  G  T  D  P  G

601 GACGTCGTCATTGAGGAGCTGTTCAATCGTATACCGGAAACAAGCGTATGGAATGAGAAC
      D  V  V  I  E  E  L  F  N  R  I  P  E  T  S  V  W  N  E  N

661 GAACGCGTCCTGTCGAACGCCAACCATCTAGTGTCCACAGCATTGTGGCGTAATGAGCAG
      E  R  V  L  S  N  A  N  H  L  V  S  T  A  L  W  R  N  E  Q

721 AGCTTCCGCGTGGAGTCGGAGCTGGGCGAGCGTCCAAGGACGCTAGTCAGAGGCCCAGTG
      S  F  R  V  E  S  E  L  G  E  R  P  R  T  L  V  R  G  P  V

781 CTCCGCGACGACGGCTCGTATATCTGTCTCGAGGCGACCGACCAGGAGACAGGAGAACCA
      L  R  D  D  G  S  Y  I  C  L  E  A  T  D  Q  E  T  G  E  P

841 CTTGAGGTGCACGTTCCATATTTCACGGAACGGCCGCCTTCCAACGCGATCAAGCAGTTG
      L  E  V  H  V  P  Y  F  T  E  R  P  P  S  N  A  I  K  Q  L
```

FIG. 2A

```
 901 AGCGAGCAGGTGCTGCGCCTACGCTTGCTACGAGGCATCAAAAACCAGAGGCAAGCCAAG
      S  E  Q  V  L  R  L  R  L  L  R  G  I  K  N  Q  R  Q  A  K

961 GCGTATCTCAGATTTATATTCCCCATCGATTTGGTGAAGGACCCAAAGAAAAGGAAGATG
      A  Y  L  R  F  I  F  P  I  D  L  V  K  D  P  K  K  R  K  M

1021 ATCCGGGTTCGCTTAGATGAGAGGGATATGTGGGTCTTGAGCAGATTCTTTCTGTATCCC
      I  R  V  R  L  D  E  R  D  M  W  V  L  S  R  F  F  L  Y  P

1081 CGAATGCAGAGTAACCTTCATATTCTTGGAGACGTCCTACTGAGTCATTCCTCAACACAC
      R  M  Q  S  N  L  H  I  L  G  D  V  L  L  S  H  S  S  T  H

1141 AAGTCCCTCGTGCACCACGCTCGGTTGCAGCTCACGCTTCAGCTCATAAGGTTGGCCGCG
      K  S  L  V  H  H  A  R  L  Q  L  T  L  Q  L  I  R  L  A  A

1201 AGTCTCCAGCACTATGGCCTTGTGCATGCCGATTTTCAAGTCAGGAATATCCTGTTAGAC
      S  L  Q  H  Y  G  L  V  H  A  D  F  Q  V  R  N  I  L  L  D

1261 CAGCGTGGTGGCGTGTTTTTGACCGGCTTTGAACATCTGGTGCGAGACGGCGCCAGTGCG
      Q  R  G  G  V  F  L  T  G  F  E  H  L  V  R  D  G  A  S  A

1321 GTGTCGCCCATCGGTCGAGGATTTGCCCCGCCGGAGACTACAGCGGAACGAATGCTCCCC
      V  S  P  I  G  R  G  F  A  P  P  E  T  T  A  E  R  M  L  P

1381 TACCGCCAGCACCACCCAACGCTGATGACATTTCCGTTTGATACATGGACATTGGGGTTG
      Y  R  Q  H  H  P  T  L  M  T  F  P  F  D  T  W  T  L  G  L

1441 GCGATCTACTGGATTTGGTGCGCCGATTTGCCCAATACCGAGGACGCGGAGCTAGGCGGA
      A  I  Y  W  I  W  C  A  D  L  P  N  T  E  D  A  E  L  G  G

1501 ATTGAATGGATCTATCGACGCTGCAAGAATATCCCACAGCCAGTCAGAGCTTTGCTTGAG
      I  E  W  I  Y  R  R  C  K  N  I  P  Q  P  V  R  A  L  L  E

1561 GGATTCTTGCGATACTCGAAAGAGGATCGGGCTCCTCCCATTGCAAGCCATGGAGACTTC
      G  F  L  R  Y  S  K  E  D  R  A  P  P  I  A  S  H  G  D  F

1621 TGAGTACGAGCAACTGCGCACAGAGCTATCAGCCGTTTTGCCCCTGTATCAAACTGATGG

1681 AGAACCGGCATGAGAGGGTGGCGCGCCACCATCGGGAACATCTCAGCCGGACGAAGCTGG

1741 AGCCGCTGAGGCGGTTACGGCAATCTAGAACCTCGAGGAGGGGCCAGCGATGAGCTTGAA

1801 TTC
```

FIG. 2B

SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 537 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO: 1:

```
Glu Asn Cys Ala Ser Val Arg Ser Ser Cys Leu Ile Trp Leu Ala
1               5                   10                  15

Ala Ala Phe Phe Val Ser Ala Leu Gly His Val Gln Gln Gly Ala Gly
            20                  25                  30

Val Val Arg Pro Arg His Trp Gln Asn Ser Glu Ala Ala Val Ser Val
            35                  40                  45

Arg Pro Pro Gly Gly Ala Ser Pro Arg His Phe His Ser Pro Ile Glu
        50                  55                  60

Pro Val Ala Phe Ile Asp Gly Glu His Val Glu Asp Lys His Gly Gly
65                      70                  75                  80

Ser Trp Leu Glu Gln Glu Ala Ala Glu Glu Val Thr Pro Leu Leu Asn
                    85                  90                  95

Ser His Thr Glu Thr Pro Thr Gln Ser Pro Ser Ala Phe Arg Arg Leu
                100                 105                 110

Leu Arg Arg Leu Arg Phe Trp Arg Arg Gly Arg Thr Gly Gly Ser Asp
            115                 120                 125

Gly Gly Gly Glu Pro Pro Gln Thr Pro Arg Pro Ser Leu Pro Thr Arg
        130                 135                 140

Leu Phe Gln His Leu Arg Arg Ala Ala Ala Ile Pro Ala Ala Ala
145                 150                 155                 160

Ser Arg Phe Phe Arg Arg Phe Arg Arg Val Gln Glu Pro Val Phe Pro
                165                 170                 175
```

```
Pro Asp Glu Phe Pro Glu Asp Val Asp Thr Asn Pro Met Tyr Phe Arg
            180                 185                 190

Gly Thr Asp Pro Gly Asp Val Val Ile Glu Glu Leu Phe Asn Arg Ile
        195                 200                 205

Pro Glu Thr Ser Val Trp Asn Glu Asn Glu Arg Val Leu Ser Asn Ala
    210                 215                 220

Asn His Leu Val Ser Thr Ala Leu Trp Arg Asn Glu Gln Ser Phe Arg
225                 230                 235                 240

Val Glu Ser Glu Leu Gly Glu Arg Pro Arg Thr Leu Val Arg Gly Pro
                245                 250                 255

Val Leu Arg Asp Asp Gly Ser Tyr Ile Cys Leu Glu Ala Thr Asp Gln
            260                 265                 270

Glu Thr Gly Glu Pro Leu Glu Val His Val Pro Tyr Phe Thr Glu Arg
        275                 280                 285

Pro Pro Ser Asn Ala Ile Lys Gln Leu Ser Glu Gln Val Leu Arg Leu
    290                 295                 300

Arg Leu Leu Arg Gly Ile Lys Asn Gln Arg Gln Ala Lys Ala Tyr Leu
305                 310                 315                 320

Arg Phe Ile Phe Pro Ile Asp Leu Val Lys Asp Pro Lys Lys Arg Lys
                325                 330                 335

Met Ile Arg Val Arg Leu Asp Glu Arg Asp Met Trp Val Leu Ser Arg
            340                 345                 350

Phe Phe Leu Tyr Pro Arg Met Gln Ser Asn Leu His Ile Leu Gly Asp
        355                 360                 365

Val Leu Leu Ser His Ser Ser Thr His Lys Ser Leu Val His His Ala
    370                 375                 380

Arg Leu Gln Leu Thr Leu Gln Leu Ile Arg Leu Ala Ala Ser Leu Gln
385                 390                 395                 400

His Tyr Gly Leu Val His Ala Asp Phe Gln Val Arg Asn Ile Leu Leu
                405                 410                 415

Asp Gln Arg Gly Gly Val Phe Leu Thr Gly Phe Glu His Leu Val Arg
            420                 425                 430

Asp Gly Ala Ser Ala Val Ser Pro Ile Gly Arg Gly Phe Ala Pro Pro
        435                 440                 445

Glu Thr Thr Ala Glu Arg Met Leu Pro Tyr Arg Gln His His Pro Thr
    450                 455                 460

Leu Met Thr Phe Pro Phe Asp Thr Trp Thr Leu Gly Leu Ala Ile Tyr
465                 470                 475                 480

Trp Ile Trp Cys Ala Asp Leu Pro Asn Thr Glu Asp Ala Glu Leu Gly
                485                 490                 495

Gly Ile Glu Trp Ile Tyr Arg Arg Cys Lys Asn Ile Pro Gln Pro Val
            500                 505                 510

Arg Ala Leu Leu Glu Gly Phe Leu Arg Tyr Ser Lys Glu Asp Arg Ala
        515                 520                 525

Pro Pro Ile Ala Ser His Gly Asp Phe
    530                 535
```

(2) INFORMATION FOR SEQ ID NO: 2:

(i) SEQUENCE CHARACTERISTICS:
        (A) LENGTH: 1803 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 2:

```
GAATTCGGGG AAAACTGTGC GTCGGTCAGA TCATCGTCGT GTCTTATCTG GCTAGCTGCC        60

GCATTCTTTG TTTCGGCACT TGGCCACGTA CAGCAAGGCG CTGGCGTTGT GCGGCCTCGC       120

CACTGGCAGA ACTCGGAAGC CGCTGTTAGT GTCCGGCCGC CGGGAGGCGC GTCCCCTAGA       180

CATTTCCACA GCCCAATTGA GCCAGTAGCA TTTATTGATG GGGAGCACGT TGAAGACAAG       240

CATGGAGGCT CATGGCTGGA GCAGGAAGCG GCCGAGGAAG TGACCCCCTT ACTGAACAGC       300

CACACAGAGA CCCCGACACA GTCCCCCAGT GCTTTTAGAA GGTTACTCAG GCGTTTGCGT       360

TTTTGGCGAC GTGGGAGGAC AGGCGGATCA GATGGCGGAG GAGAACCACC GCAGACGCCT       420

CGCCCTTCCC TACCGACCCG ACTGTTTCAG CATTTGCGGC GTGCGGCAGC AGCAATTCCC       480

GCGGCGGCAT CTAGATTCTT TAGGAGATTT CGACGAGTCC AAGAACCTGT ATTCCCTCCC       540

GACGAGTTTC CGGAGGATGT CGACACGAAC CCTATGTATT TCCGCGGTAC GGATCCTGGA       600

GACGTCGTCA TTGAGGAGCT GTTCAATCGT ATACCGGAAA CAAGCGTATG GAATGAGAAC       660

GAACGCGTCC TGTCGAACGC CAACCATCTA GTGTCCACAG CATTGTGGCG TAATGAGCAG       720

AGCTTCCGCG TGGAGTCGGA GCTGGGCGAG CGTCCAAGGA CGCTAGTCAG AGGCCCAGTG       780

CTCCGCGACG ACGGCTCGTA TATCTGTCTC GAGGCGACCG ACCAGGAGAC AGGAGAACCA       840

CTTGAGGTGC ACGTTCCATA TTTCACGGAA CGGCCGCCTT CCAACGCGAT CAAGCAGTTG       900

AGCGAGCAGG TGCTGCGCCT ACGCTTGCTA CGAGGCATCA AAAACCAGAG GCAAGCCAAG       960

GCGTATCTCA GATTTATATT CCCCATCGAT TTGGTGAAGG ACCCAAAGAA AAGGAAGATG      1020

ATCCGGGTTC GCTTAGATGA GAGGGATATG TGGGTCTTGA GCAGATTCTT TCTGTATCCC      1080

CGAATGCAGA GTAACCTTCA TATTCTTGGA GACGTCCTAC TGAGTCATTC CTCAACACAC      1140

AAGTCCCTCG TGCACCACGC TCGGTTGCAG CTCACGCTTC AGCTCATAAG GTTGGCCGCG      1200

AGTCTCCAGC ACTATGGCCT TGTGCATGCC GATTTTCAAG TCAGGAATAT CCTGTTAGAC      1260

CAGCGTGGTG GCGTGTTTTT GACCGGCTTT GAACATCTGG TGCGAGACGG CGCCAGTGCG      1320

GTGTCGCCCA TCGGTCGAGG ATTTGCCCCG CCGGAGACTA CAGCGGAACG AATGCTCCCC      1380

TACCGCCAGC ACCACCCAAC GCTGATGACA TTTCCGTTTG ATACATGGAC ATTGGGGTTG      1440

GCGATCTACT GGATTTGGTG CGCCGATTTG CCCAATACCG AGGACGCGGA GCTAGGCGGA      1500

ATTGAATGGA TCTATCGACG CTGCAAGAAT ATCCCACAGC CAGTCAGAGC TTTGCTTGAG      1560

GGATTCTTGC GATACTCGAA AGAGGATCGG GCTCCTCCCA TTGCAAGCCA TGGAGACTTC      1620

TGAGTACGAG CAACTGCGCA CAGAGCTATC AGCCGTTTTG CCCCTGTATC AAACTGATGG      1680

AGAACCGGCA TGAGAGGGTG GCGCGCCACC ATCGGGAACA TCTCAGCCGG ACGAAGCTGG      1740

AGCCGCTGAG GCGGTTACGG CAATCTAGAA CCTCGAGGAG GGGCCAGCGA TGAGCTTGAA      1800

TTC                                                                   1803
```

CLONING AND EXPRESSION OF A PROTEIN ANTIGEN OF *TOXOPLASMA GONDII*

This is a continuation of application Ser. No. 08/075,571, filed 16 Jun. 1993, now abandoned, which application is a U.S. National Stage application corresponding to application No. PCT/EP91/02423, which was filed according to the Paris Convention Treaty on Dec. 16, 1991, claiming benefit from Great Britain application No. 9027728.6, filed Dec. 20, 1990.

This invention relates to a novel protein capable of inducing an immune response protective against infection caused by *Toxoplasma gondii* and to the cloning and expressing of a gene encoding the said protein. The invention further relates to novel vaccines and novel in-vitro diagnostic methods and kits comprising the said protein and to their use.

*Toxoplasma gondii* is an ubiquitous obligate intracellular protozoan parasite which infects mammals and birds. Although toxoplasmosis is generally clinically asymptomatic in healthy individuals, it may cause severe complications in pregnant women and immunocompromised patients. If primary infection occurs during pregnancy, transplacental transmission can lead to abortion or neonatal malformations [for reviews see Remington and Krahenbuhl, 1982; Hughes, 1985]. In AIDS patients, *Toxoplasma* is recognized as a major opportunistic pathogen. In such immunodeficient individuals, rupture of cysts which persist in the tissues of the host after a primary infection and release of proliferative forms of the parasite may cause severe disseminated toxoplasmosis and/or encephalitis. In approximately 30 percent of *Toxoplasma*-antibody-positive patients with AIDS, toxoplasmic encephalitis will develop due to reactivation of their latent infection. Thus, about 25 percent of patients with AIDS in Belgium, France, and Germany and 5 to 10 percent of such patients in the United States will contract toxoplasmic encephalitis (McCabe and Remington, 1988).

The fetus and the newborn are very sensitive to toxoplasmosis. Infection of the mother during pregnancy and transmission to the fetus can lead to miscarriage, birth of abnormal children (especially with ocular and cerebral lesions), or birth of apparently normal children who will develop grave sequelae months or years later (blindness, mental retardation). Current estimates indicate that 0.1 to 0.9% of newborns are afflicted with congenital toxoplasmosis.

Besides its negative impact on human health, the parasite is also detrimental in sheep and pig farming since abortions resulting from the infection lead to relatively important economic losses [Beverley, 1976]. A vaccine for controlling this infectious agent would be of great value and the feasibility of its development is suggested by the fact that primary infection with *Toxoplasma* results in specific and long-lasting immunity against reinfection [Remington and Krahenbuhl, 1982]. However, no effective and safe vaccine is currently available against toxoplasmosis. The best available vaccine candidate is a temperature- sensitive mutant of the highly virulent RH strain (Pfefferkorn and Pfefferkorn, 1976). This mutant, named ts-4, is currently being tested in animals as a live vaccine (Waldeland and Frenkel, 1983, Waldeland et al., 1983, Frenkel and Escajadillo, 1987). However, this potential vaccine has two main drawbacks.

First because it is derived from a highly virulent strain, the possibility of reversion has to be taken into account in the evaluation of safety.

Second and more importantly, because this vaccine consists of the live tachyzoite form of the parasite which is very unstable in an extracellular environment, the lack of stability of the vaccine preparation will hamper its distribution and administration. Thus, a safer sub-unit vaccine is clearly needed.

In response to infection, immunocompetent hosts mount an immune response, the humoral component of which underlies the methods generally used in toxoplasmosis diagnosis. The immune response also confers protection against subsequent infection to host: women showing serological evidence of previous infection before the beginning of pregnancy are at no risks of transmitting toxoplasmosis to their fetus.

The immune response against *T. gondii* involves both humoral and cellular components [Remington and Krahenbuhl, 1982]. However, in-vitro and in-vivo studies have indicated that cell-mediated immunity plays an essential role in protection and have identified interferon-gamma (IFN-gamma) as the major mediator of resistance [Frenkel, 1967; Nathan et al., 1984; Pfefferkorn, 1984; Sethi et al., 1985; Suzuki and Remington, 1988, Suzuki et al., 1988, 1989; Suzuki and Remington, 1990].

When cell-mediated immunity is essential for protection, as it is the case in toxoplasmosis, the identification of pathogen antigen(s) involved in the activation of the protective immune mechanism must be done at the T-cell level. During the last five years, the need for better prophylactic means to control tuberculosis and leprosy, two bacterial-borne infectious diseases in which protective immunity is also cell-mediated, stimulated the development of new strategies and techniques to identify T-cell antigens. One of them is the so-called "T-cell blot technique" in which antigens of the pathogen are size-fractionated in a denaturing polyacrylamide gel, blotted to nitrocellulose and then tested for reactivity with T-cells of immune or vaccinated subjects [Lamb and Young, 1987]. Another approach makes use of antigens of the pathogen cloned and expressed in *E. coli*, which are also tested for their T-cell reactivity [Mustafa et al. 1986]. However, in this latter approach, the tested antigen had been previously identified and selected with mouse monoclonal antibodies. The main limitation of this strategy is that human T-cells may not necessarily react with the same antigen as do a limited subset of mouse antibodies. To overcome this problem, an approach involving testing pools of recombinants from a whole library for reactivity with T-cell clones was proposed and allowed the identification of a previously undetected mycobacterial antigen [Mustafa et al., 1988]. However, this method becomes impractical in the case of more complex organisms.

As described herein, we show that T-cell antigens of eukaryotic pathogens can be identified through cloning of their cDNA in a bacterial expression vector ($\lambda$gt11), screening the obtained library with a pool of sera from immune subjects, and testing the whole set of antibody-preselected recombinant antigens in the form of crude lysates for reactivity with a T-cell clone (TLC) derived from an immune subject.

Using this approach we have identified a 54-kDa antigen of *T. gondii* recognized by a human TLC which is of potential value as a vaccine against infection caused by *T. gondii*.

Where reference is made to a 54-kDa antigen or protein it should be understood to be to an approximately 54-kDa protein as determined by Western blotting as herein described.

To assist in understanding the invention reference is made to the Figures hereinbelow in which:

FIG. 1 shows the sequencing strategy for a cDNA clone known as Tg34. The map of the restriction sites of the Tg34

EcoRI insert used for the construction of unidirectional deletion clones in pBluescript KS⁺and the localization of the sequences corresponding to the synthesized internal oligonucleotide primers ( ) are shown. The arrows represent the length and direction of the nucleotide sequence readings.

FIGS. 2A and 2B show the nucleotide and deduced amino acid sequence of the Tg34 cDNA clone. The sense strand sequence and the deduced amino acid sequence of the single long open reading frame (1620 bp) are displayed. The stop codon is boxed. Sequences predicted to fold as transmembrane helices are underlined and a potential signal sequence cleavage site is shown as an open triangle.

The present invention provides a 54-kDa protein which is reactive with antibodies raised against the recombinant protein having the sequence shown in FIG. 2 or reactive with antibodies obtained by absorption from human serum on the recombinant protein shown in FIG. 2, and immunogenic derivatives (including mutants) thereof.

It will be understood that the 54-kDa protein according to the invention is purified and or synthetic material and does not encompass the 'natural' 54-kDa of *T. gondii*. Preferably the 54-kDa antigen is over 60% pure, more preferably over 70% typically 80–100% especially 90–100% pure.

The term "immunogenic derivative" encompasses any molecule such as a truncated or other derivative of the protein which retains the ability to induce an immune response to the protein following internal administration to a human or to an animal or which retains the ability to react with antibodies present in the sera or other biological samples of *Toxoplasma gondii*-infected humans or animals. Such other derivatives can be prepared by the addition, deletion, substitution, or rearrangement of amino acids or by chemical modifications thereof.

Immunogenic fragments of the protein, which may be useful in the preparation of subunit vaccines or diagnostic tests, may be prepared by expression of the appropriate gene fragments or by peptide synthesis, for example using the Merrifield synthesis (The Peptides, Vol 2., Academic Press, NY, page 3).

The immunogenic derivative of the invention can be a hybrid, that is, a fusion polypeptide containing additional sequences which can carry one or more epitopes for other *T. gondii* immunogens, or other non-*T. gondii* immunogens. Alternatively, the immunogenic derivative of the invention can be fused to a carrier polypeptide which has immunostimulating properties, as in the case of an adjuvant, or which otherwise enhances the immune response to the 54-kDa protein or derivative thereof, or which is useful in expressing, purifying or formulating the 54-kDa protein or derivative thereof.

The invention also extends to the 54-kDa protein or immunogenic derivative thereof when chemically conjugated to a macromolecule using a conventional linking agent such as glutaraldehyde (Geerlings et al, (1988) *J. Immunol. Methods*, 106, 239–244).

A further aspect of the invention provides a process for the preparation of the 54-kDa protein or an immunogenic derivative thereof according to the invention, which process comprises expressing DNA encoding said protein or derivative thereof in a recombinant host cell and recovering the product, and thereafter, optionally, preparing a derivative thereof.

A DNA molecule comprising such coding sequence forms a further aspect of the invention and can be synthesized by standard DNA synthesis techniques, such as by enzymatic ligation as described by D. M. Roberts et al in *Biochemistry* 1985, 24, 5090–5098, by chemical synthesis, by in vitro enzymatic polymerization, or by a combination of these techniques.

Enzymatic polymerisation of DNA may be carried out in vitro using a DNA polymerase such as DNA polymerase I (Klenow fragment) in an appropriate buffer containing the nucleoside triphosphates dATP, dCTP, dGTP and dTTP as required at a temperature of 10°–37° C., generally in a volume of 50 μl or less. Enzymatic ligation of DNA fragments may be carried out using a DNA ligase such as T4 DNA ligase in an appropriate buffer, such as 0.05M Tris (pH 7.4), 0.01M $MgCl_2$, 0.01M dithiothreitol, 1 mM spermidine, 1 mM ATP and 0.1 mg/ml bovine serum albumin, at a temperature of 4° C. to ambient, generally in a volume of 50 μl or less. The chemical synthesis of the DNA polymer or fragments may be carried out by conventional phosphotriester, phosphite or phosphoramidite chemistry, using solid phase techniques such as those described in 'Chemical and Enzymatic Synthesis of Gene Fragments—A Laboratory Manual' (ed. H. G. Gassen and A. Lang), Verlag Chemie, Weinheim (1982), or in other scientific publications, for example M. J. Gait, H. W. D. Matthes, M. Singh, B. S. Sproat, and R. C. Titmas, *Nucleic Acids Research*, 1982, 10, 6243; B. S. Sproat and W. Bannwarth, *Tetrahedron Letters*, 1983, 24, 5771; M. D. Matteucci and M. H. Caruthers, *Tetrahedron Letters*, 1980, 21, 719; M. D. Matteucci and M. H. Caruthers, *Journal of the American Chemical Society*, 1981, 103, 3185; S. P. Adams et al., *Journal of the American Chemical Society*, 1983, 105, 661; N. D. Sinha, J. Biernat, J. McMannus, and H. Koester, *Nucleic Acids Research*, 1984, 12, 4539; and H. W. D. Matthes et al., *EMBO Journal*, 1984, 3, 801.

Alternatively, the coding sequence can be derived from *T. gondii* mRNA, using known techniques (e.g. reverse transcription of mRNA to generate a complementary cDNA strand), and commercially available cDNA kits.

The invention is not limited to the specifically disclosed sequence, but includes all molecules coding for the 54-kDa protein or an immunogenic derivative thereof, as described above.

Accordingly the invention provides a recombinant DNA molecule comprising:

(a) at least a portion of a DNA sequence represented by the sequence shown in FIG. 2;

(b) a DNA sequence which is degenerate as a result of the genetic code to the above sequence; or (c) a DNA sequence which hybridises under stringent conditions to the complementary sequence of the above sequence;

the said recombinant DNA molecule encoding a protein:

(i) capable of being recognised by antibodies in the sera or other biological samples of *T.gondii* infected humans and animals; or (ii) capable of raising antibodies following internal administration to a human or animal.

The invention also provides a recombinant DNA molecule comprising the complementary sequence of the sequence defined under (a) (b) or (c) above.

The invention also relates to nucleic acids comprising nucleotide sequences which hybridize with the above mentioned nucleotide sequences under the following stringent hybridization conditions:

hybridization medium: a preferred hybridization medium contains about 5×SSPE (SSPE=0.18M NaCl, 0.01M sodium phosphate, 0.001 ethylenedinitrilo tetraacetic acid pH 7.7), 0.1% bovine serum albumin, 0.1% Ficoll, 0.1% polyvinylpyrrolidone, 0.5% sodium dodecylsulfate and about 0.1 mg/ml sheared denatured salmon sperm DNA, wash medium: a preferred wash medium contains about 1×SSPE, 0.1 sodium dodecylsulfate, hybridization temperature (HT) and wash temperature (WT) for the nucleic acids of the invention are HT=WT=65° C. These temperatures are to be considered as approximately ±5° C.

It is also to be noted that in the above defined nucleic acids, as well as in the hereafter defined nucleic acids, the nucleotide sequences which are brought into play are such that T can be replaced by U.

DNA which encodes mutants of the 54-kDa protein may be prepared by site-directed mutagenesis of the cDNA which codes for the 54-kDa protein by conventional methods such as those described by G. Winter et al in *Nature* 1982, 299, 756–758 or by Zoller and Smith 1982; *Nucl. Acids Res.*, 10, 6487–6500, or deletion mutagenesis such as described by Chan and Smith in *Nucl. Acids Res.*, 1984, 12, 2407–2419 or by G. Winter et al in *Biochem. Soc. Trans.*, 1984, 12, 224–225.

The process of the invention may be performed by conventional recombinant techniques such as described in Maniatis et. al., Molecular Cloning—A Laboratory Manual; Cold Spring Harbor, 1982–1989.

In particular, the process may comprise the steps of:

i) preparing a replicable or integrating expression vector capable, in a host cell, of expressing a DNA polymer comprising a nucleotide sequence that encodes said 54-kDa protein or an immunogenic derivative thereof;

ii) transforming a host cell with said vector;

iii) culturing said transformed host cell under conditions permitting expression of said DNA polymer to produce said protein; and iv) recovering said protein.

The term 'transforming' is used herein to mean the introduction of foreign DNA into a host cell by transformation, transfection or infection with an appropriate plasmid or viral vector using e.g. conventional techniques as described in *Genetic Engineering;* Eds. S. M. Kingsman and A. J. Kingsman; Blackwell Scientific Publications; Oxford, England, 1988. The term 'transformed' or 'transformant' will hereafter apply to the resulting host cell containing and expressing the foreign gene of interest.

The expression vector is novel and also forms part of the invention.

The replicable expression vector may be prepared in accordance with the invention, by cleaving a vector compatible with the host cell to provide a linear DNA segment having an intact replicon, and combining said linear segment with one or more DNA molecules which, together with said linear segment encode the desired product, such as the DNA polymer encoding the 54-kDa protein, or fragments thereof, under ligating conditions.

Thus, the DNA polymer may be preformed or formed during the construction of the vector, as desired.

The choice of vector will be determined in part by the host cell, which may be prokaryotic or eukaryotic. Suitable vectors include plasmids, bacteriophages, cosmids and recombinant viruses.

The preparation of the replicable expression vector may be carried out conventionally with appropriate enzymes for restriction, polymerisation and ligation of the DNA, by procedures described in, for example, Maniatis et al cited above.

The recombinant host cell is prepared, in accordance with the invention, by transforming a host cell with a replicable expression vector of the invention under transforming conditions. Suitable transforming conditions are conventional and are described in, for example, Maniatis et al cited above, or "DNA Cloning" Vol. II, D. M. Glover ed., IRL Press Ltd, 1985.

The choice of transforming conditions is determined by the host cell. Thus, a bacterial host such as *E. coli* may be treated with a solution of $CaCl_2$ (Cohen et al, *Proc. Nat. Acad. Sci.,* 1973, 69, 2110) or with a solution comprising a mixture of RbCl, $MnCl_2$, potassium acetate and glycerol, and then with 3-[N-morpholino]-propane-sulphonic acid, RbCl and glycerol. Mammalian cells in culture may be transformed by calcium co-precipitation of the vector DNA onto the cells. The invention also extends to a host cell transformed with a replicable expression vector of the invention.

Culturing the transformed host cell under conditions permitting expression of the DNA polymer is carried out conventionally, as described in, for example, Maniatis et al and "DNA Cloning" cited above. Thus, preferably the cell is supplied with nutrient and cultured at a temperature below 45° C.

The product is recovered by conventional methods according to the host cell. Thus, where the host cell is bacterial, such as *E. coli* it may be lysed physically, chemically or enzymatically and the protein product isolated from the resulting lysate. Where the host cell is mammalian, the product may generally be isolated from the nutrient medium or from cell free extracts. Conventional protein isolation techniques include selective precipitation, absorption chromatography, and affinity chromatography including a monoclonal antibody affinity column.

Preferably, the host cell is *E. coli*. Alternatively, the expression may be carried out in insect cells using a suitable vector such as the Baculovirus.

The novel protein of the invention may also be expressed in yeast cells.

The vaccine of the invention comprises an immunoprotective amount of the 54-kDa protein or an immunogenic derivative thereof according to the invention. The term "immunoprotective" refers to the amount necessary to elicit an immune response against a subsequent *T. gondii* challenge such that disease is averted or mitigated, and/or transmision of the disease is blocked or delayed. In the vaccine of the invention, an aqueous solution of the protein can be used directly. Alternatively, the protein, with or without prior lyophilization, can be mixed or absorbed with any of the various known adjuvants. Such adjuvants include, but are not limited to, aluminium hydroxide, muramyl dipeptide and saponins such as Quil A. As a further exemplary alternative, the protein can be encapsulated within microparticles such as liposomes. In yet another exemplary alternative, the protein can be conjugated to an immunostimulating macromolecule, such as killed *Bordetella* or a tetanus toxoid.

Vaccine preparation is generally described in New Trends and Developments in Vaccines, Voller et al. (eds.), University Park Press, Baltimore, Md., 1978. Encapsulation within liposomes is described by Fullerton, U.S. Pat. No. 4,235, 877. Conjugation of proteins to macromolecules is disclosed, for example, by Likhite, U.S. Pat. No. 4,372,945 and Armor et al., U.S. Pat. No. 4,474,757.

Use of Quil A is disclosed by Dalsgaard et al., *Acta Vet Scand*, 18:349 (1977).

The amount of the protein of the present invention present in each vaccine dose is selected as an amount which induces an immunoprotective response without significant, adverse side effects in typical vaccines. Such amount will vary depending upon which specific immunogen is employed and whether or not the vaccine is adjuvanted. Generally, it is expected that each dose will comprise 1–1000 μg of protein, preferably 1–200 μg. An optimal amount for a particular vaccine can be ascertained by standard studies involving observation of antibody titres and other responses in subjects. Following an initial vaccination, subjects will preferably receive a boost in about 4 weeks, followed by repeated boosts every six months for as long as a risk of infection exists.

A further aspect of the invention provides a method of preventing *T. gondii* infections in humans, or preventing congenital transmission in humans or animals, which method comprises administering to a subject or animal in need thereof an immunogenically effective amount of the 54-kDa protein or of an immunogenic derivative thereof, or of a vaccine in accordance with the invention.

The invention also relates to a process for detecting in-vitro antibodies related to *Toxoplasma* in a human or animal biological sample liable to contain them, this process comprising incubating the biological sample, liable to contain antibodies against the parasite, with a suitable amount of the 54-kDa protein or of an immunogenic derivative thereof according to the invention under conditions which allow the formation of an antigen-antibody complex and the in-vitro detection of the antigen-antibody complex which may be formed.

Preferably, the biological medium is constituted by human serum.

The detection can be carried out according to any classical process.

By way of example a preferred method brings into play an immunoenzymatic process according to ELISA technique as described for example by Engvall, E. and Perlmann, P., *Immunochemistry*, 8:871–874, or radioimmunological or immunofluorescent or immunochemiluminescent techniques or the equivalent ones.

Such a method for detecting in-vitro antibodies related to toxoplasmosis comprises for instance the following steps:

deposit of determined amounts of the 54-kDa protein or of an immunogenic derivative thereof according to the invention in the wells of a titration microplate, generally this amount will comprise 0.1 to 1 μg of protein.

introduction into said wells of increasing dilutions of the biological sample to be tested, incubation of the microplate, repeated rinsing of the microplate, introduction into the wells of the microplate of labelled antibodies against the immunoglobulins of the animal species from which the biological sample was derived, the labelling of these antibodies being carried out by means of an enzyme which is selected from among the ones lo which are able to hydrolyze a substrate and modify the absorption or emission of light by this latter at least at a given wavelength, detection and quantification by comparing with a control standard of the amount of hydrolysed substrate.

The invention also relates to a method for the in-vitro diagnosis of toxoplasmosis, including congenital toxoplasmosis, in a patient liable to be infected by *Toxoplasma gondii* comprising:

contacting a biological sample taken from a patient with the 54-kDa protein of the invention or a derivative thereof according to the invention, under conditions enabling an in-vitro immunological reaction between said protein or immunogenic derivative and the antibodies which are possibly present in the biological sample and the in-vitro detection of the antigen-antibody complex which has possibly been formed.

To carry out the in-vitro diagnostic method for toxoplasmosis in a patient liable to be infected by *Toxoplasma gondii*, the following items or kit can be used, said items or kit comprising:

the 54-kDa protein or an immunogenic derivative according to the invention, reagents for making a medium appropriate for the immunological reaction to occur, reagents enabling detection of the antigen-antibody complex which has been produced by the immunological reaction, said reagents containing a label detectable by physico-chemical measurement methods, such as those known in the art.

The examples which follow are illustrative but not limiting of the invention.

EXAMPLES

A. MATERIALS AND METHODS

A.1. Reagents and cell culture medium

Bovine serum albumin (BSA), polyoxyethylenesorbitan monolaurate (Tween 20), diaminobenzidine, nitro blue tetrazolium, and 5-bromo-4-chloro-3-indolyl-phosphate were obtained from Sigma (St. Louis, Mo., USA). Isopropyl-β-thiogalactopyranoside (IPTG), anti-β-galactosidase monoclonal antibody (MAb) and *E. coli* strains Y1090(r–) and Y1089(r–) were purchased from Promega (Leiden, The Netherlands). EcoRI linker (d5'-CCGAATTCGG-3') was from Bethesda Research Laboratories (BRL, Gaithersburg, Md., USA). T4 DNA ligase and T4 DNA polymerase were from Boehringer Mannheim (Brussels, Belgium). Restriction enzymes were from Boehringer Mannheim or New England Biolabs (Beverly, Mass., USA) and were used according to the manufacturer's recommendations. Reagents for cell culture were obtained from Sigma, Flow Laboratories (Brussels, Belgium) or GIBCO (Ghent, Belgium). Fetal bovine serum was purchased from Sera Lab (Crawley Down, Sussex, England). Anti-HLA-DR (clone L243), anti-Leu-10 (anti-HLA-DQ, clone SK10), and anti-HLA-DP (clone B7/21) MAbs were obtained in purified form from Becton Dickinson (Erembodegem, Belgium). For inhibition experiments, they were dialyzed extensively against RPMI culture medium to eliminate sodium azide and sterile filtered.

A.2. Parasites and antigens

The RH [Sabin, 1941] and Wiktor [Francois et al., 1963] strains of *T. gondii* were maintained by serial passage in the peritoneal cavity of Swiss mice and tachyzoites were either collected from the peritoneal cavity of mice or grown in-vitro in African Green Monkey Kidney Cells (AGMK cells, Flow Laboratories) as described by Hughes et al. (1984). Briefly, $3 \times 10^7$ freshly obtained tachyzoites were used to inject a confluent culture of AGMK cells in a 150cm$^2$ culture flask. Two days later, virtually all the host cells had lysed and the tachyzoites were harvested, washed 3×with PBS and stored at −80° C.

The Gangji strain was isolated in 1984 at the Pasteur Institute of Brabant from the placenta of a woman who seroconverted during pregnancy. This strain induces a chronic infection in the mouse and has been maintained by passage of brain suspension from chronically infected mice into the peritoneum of fresh mice at one-year intervals. Gangji strain tachyzoites were collected from the peritoneal cavity of mice infected 6–8 days earlier with a cyst-containing brain suspension and treated with cortisone [De Meuter et al., 1975]. After washing, tachyzoites were stored at −80° C. until use. The soluble fraction of the sonicates of tachyzoites (F3) and of peritoneal exudate of control uninfected mice was prepared as described below.

A.3 Preparation of soluble antigenic fraction F3

$2 \times 10^9$ purified RH tachyzoites were suspended in 10 ml of PBS pH 7.2+5 mM PMSF, sonicated on ice for 5 min at 50 W (Labsonic 2000, Braun) and centrifuged at 100,000 g at 4–10° C. for 40 min. The supernatant was saved and the pellet was resuspended by sonication in 10 ml of PBS pH 7.2. After centrifugation for 30' at 100,000 g, the supernatant was pooled with that obtained after the first centrifugation. This pool was named F3. Protein concentration in F3 was determined by the Bradford method (Protein assay, Bio-Rad, Munchen, FRG), using BSA as standard.

A.4. Immune sera and antibodies

Sera from chronically infected/immune subjects were selected among samples referred to the Pasteur Institute of Brabant for diagnostic purposes. These sera were tested by the modified Sabin-Feldman dye test [Lelong and Desmonts, 1951] and by indirect immunofluorescence with anti-human IgM-labelled antibody [Remington et al., 1968]. A pool was made up of sera containing high titers of anti-*T. gondii* IgG and no detectable IgM. A pool of sera of Balb/c mice chronically infected with the virulent Wiktor strain as described below was also used in some experiments. Both sera were depleted of anti-*E. coli* antibodies by passage through a CNBr-activated sepharose column (Pharmacia, Uppsala, Sweden) to which a mixture of lysates of induced Y1089(λgt11) lysogen and Y1090 had been bound following the manufacturer's recommendations. The IgG fraction was then isolated from the pre-absorbed sera by DEAE Affi-gel Blue gel column chromatography (Bio-Rad, Richmond, Calif., USA) following the manufacturer's instructions. Aliquots of the IgG preparations were stored at −20° C. until use.

A.5. Infection of mice

Balb/c mice were injected i.p. with $5 \times 10^4$ tachyzoites of the virulent Wiktor strain. They were given trimethoprim 1.6 mg/ml-sulfamethoxazol 8 mg/ml in drinking water for two weeks and 80 μg trimethroprim-400 μg sulfamethoxazol i.p. twice a day from day 12 to day 18. 2 of 7 mice survived the infection. Mouse No.1 was then boosted with the following doses of F3: 2 μg i.p. at day 39, 100 μg i.p. at day 42 and 100 μg i.v. at day 43. Mouse No.2 was boosted with 1 μg F3 i.p. on day 270 and 50 μg F3 i.p. and 50 μg F3 i.v. on day 274. Sera were collected at day 46 and 277 respectively.

A.6. Isolation of peripheral blood mononuclear cells (PBMC)

PBMC were isolated from heparinized blood of healthy donors by Ficoll-Paque (Pharmacia, Uppsala, Sweden) in accordance with the manufacturers' instructions. Cells were washed with Hanks' Balanced salt solution (HBSS) before further processing. For stimulation of the clones and their use as antigen presenting cells (APC) in proliferation assays, cells were irradiated (3000 rad, $^{60}$Co irradiator) and cryopreserved until use.

A.7. T-cell clones

The isolation and characterization of the human TLC specific for *T. gondii* is described below. They were derived from a chronically infected/immune donor whose seroconversion had occurred at least one year before the beginning of the study.

A.8. Isolation of human T-cell clones 1 ml PBMC ($1 \times 10^6$ cells/ml) was stimulated in-vitro with 30 μg/ml of the antigen F3 in a 24-well tissue culture plate (Costar, Cambridge, Mass., USA) and incubated at 37° C. in a humidified atmosphere containing 5% $CO_2$ in air. Seven days later, after washing, $10^5$ cells were restimulated with $5 \times 10^5$ fresh autologous irradiated PBMC, 30 μg/ml of F3, and 5 U/ml of recombinant IL-2 (rIL-2, Boehringer, Mannheim, FRG) in 1 ml of medium in 24-well plates. On day 7, blasts were recovered by Ficoll-Paque and cloned by limiting dilution (20 cells/well) in a final volume of 200 μl of medium in 96-well trays (Costar) in the presence of 5 U/ml of rIL-2 and either autologous irradiated PBMC ($10^5$ cells/well) +F3 (30 μg/ml) or allogeneic irradiated PBMC ($10^5$ cells/well) +phytohaemagglutinin (PHA, 1/100 v/v of stock solution provided by the manufacturer [Pharmacia]). One week later, medium was changed and rIL-2 was added. This step was repeated every 4 days thereafter. After 2 weeks, growing clones were screened and transfered to 24-well plates together with either autologous irradiated PBMC +F3 or allogeneic irradiated PBMC +PHA.

A.9. Maintenance of T-cell clones

The TLC have been maintained in long term culture by stimulation every 2–3 weeks in the presence of allogeneic irradiated PBMC, 1% (v:v) phytohemagglutinin, M form (PHA, GIBCO) and 5 U/ml recombinant IL-2 (rIL-2, Boehringer Mannheim) in RPMI 1640 medium supplemented with L-glutamine (2 mM), sodium pyruvate (1 mM), non-essential amino acids (0.1 mM), HEPES (15 mM), β-mercaptoethanol ($5 \times 10^{-5}$M), penicillin-streptomycin (50 IU/ml), and 10% fetal bovine serum. After 4 days, T-cells were washed and supplied with rIL-2 (5 U/ml). rIL-2 was added every 4 days. For proliferation assays, T-cells were used at least one week after restimulation and 4 days after the last rIL-2 addition.

A.10. B-lymphoblastoid cell lines (B-LCL)

The B-LCL DOC3, JAH, MS37, P5493, RAG and HID were obtained from the European Collection of Animal Cell Cultures (ECACC, Porton Down, Salisbury, UK); J1066 and J929 were obtained from the European Collection for Biomedical Research (ECBR, Istituto Nazionale per la Ricerca sul Cancro, Genova, Italy). The autologous B-LCL was isolated as previously described (Roder et al., 1986). Briefly, PBMC ($5 \times 10^5$ cells/200 μl) were incubated in culture medium containing 30% (v:v) of B 95-8 cell line supernatant for 24 h in 96 well U-bottomed culture plates. The medium was then replaced by fresh medium and after 2–3 weeks growing cultures were pooled and further expanded. Cells were irradiated (5000 rad) and cryopreserved until their use as antigen-presenting cells (APC).

A.11. Cell proliferation assay

Twenty-thousand T-cells from the clone were incubated with the appropriate concentration of antigen or antigen-bearing nitrocellulose particles in the presence of either $10^5$ cryopreserved PBMC, or $2 \times 10^4$ cryopreserved B-LCL in 96-well flat bottom plates, in a total volume of 200 μl for 72 hrs. When autologous PBMC were not available any more, PBMC, from an allogeneic donor, selected for their ability to present antigen to TLC 32 were used. The cells were pulsed with 1 μCi of [$^3$H]Thymidine (Amersham, Brussels, Belgium) for the last 18–20 h of culture and harvested onto glass-fiber filters with an automatic cell harvester. [$^3$H] thymidine incorporation was assessed by liquid scintillation spectroscopy.

A.12. Construction of *T. gondii* cDNA library in λgt11 vector

Total RNA was extracted from *T. gondii* tachyzoites (Wiktor strain) grown in AGMK cells according to the method described by Johnson et al. [1986]. Poly(A)+RNA was purified by affinity chromatography on an oligo(dT) cellulose column (Boehringer Mannheim) and ethanol-precipitated as described by Maniatis et al. [1982] cDNA was synthesized using an Amersham cDNA synthesis kit. The first strand was synthesized using reverse transcriptase and oligo(dT) primer. The second strand was synthesized using RNAse H and DNA polymerase I [Gubler and Hoffman, 1983]. After purification, the cDNA was methylated with EcoRI methylase (Promega) according to Huynh et al. [1985] and blunted with T4 DNA polymerase in standard conditions [Maniatis et al., 1982]. DNA was purified by phenol-CHCl$_3$ extraction and ethanol-precipitated. EcoRI linker phosphorylation and ligation to cDNA, digestion with EcoRI, size fractionation on Bio-Gel A-50m (Bio-Rad) column and ligation with λgt11 vector arms (Promega) were carried out according to Huynh et al. [1985]. After incubation with packaging extracts (Promega), the resulting phage particles were used to infect *E. coli* Y1090(r–); plaques containing recombinant phages were identified according to the manufacturer's recommendations.

A.13. Immunoscreening

The procedure was adapted from Huynh et al. [1985]. Y1090(r–) bacteria were infected and grown as described except that soft agarose-culture medium was used instead of soft agar-medium. Dry nitrocellulose membranes (Hybond-C, Amersham) previously saturated in 10 mM IPTG were overlayed on each plate and incubated for 3.5 h at 37° C. The membranes were removed, rinsed with washing buffer (10 mM Tris-HCl pH 8.0, 150 mM NaCl, 0.05% (v:v) Tween 20) and incubated for 2 h at room temperature (RT) in incubation buffer (1% BSA in washing buffer). They were then rinsed once and incubated (4 h or overnight) with anti-*T. gondii* human or mouse IgG (15 μg/ml or 10 μg/ml, respectively). The membranes were washed extensively and developed with one of the following reagent systems: (a) alkaline phosphatase-labelled goat anti-mouse immunoglobulin (GAM-AP, Promega, 1/5000 dilution, 2 h, RT), (b) biotinylated sheep anti-human immunoglobulin (Amersham, 1/1000 dilution, 2 h, RT), followed by streptavidin-biotin-peroxidase pre-formed complex (Amersham, 1/500 dilution, 45 min, RT), (c) a mixture of mouse MAbs against human kappa and lambda immunoglobulin light chains (0.2 μg/ml or 1/12000 ascite dilution, 2 h, RT), followed by GAM-AP (1/5000, 2 h, RT). All antibody dilutions were done in incubation buffer. After extensive washing, peroxidase activity was detected with 0.2 mg/ml diaminobenzidine, 0.02% $H_2O_2$, 100 mM Tris-HCl pH 7.6, and alkaline phosphatase activity was detected with 0.33 mg/ml nitro blue tetrazolium, 0.165 mg/ml 5-bromo-4-chloro-3- indolyl-phosphate, 100 mM NaCl, 5 mM $MgCl_2$, 100 mM Tris-HCl pH9.5. The reaction was stopped by extensive washing with $H_2O$ (peroxidase) or 10 mM EDTA (alkaline phosphatase).

A.14. Preparation of crude lysate from λgt11 lysogen

Lysogens were prepared by infection of *E. coli* Y1089(r–) with λgt11 recombinants from the cDNA library and crude lysates were prepared from these lysogens after induction with IPTG essentially as described by Huynh et al. [1985]. The cell pellet was resuspended in 1/25 of the original culture volume in phosphate buffered saline pH 7.2 and immediately frozen in liquid nitrogen. After thawing, lysis was completed by sonication at 4° C. and the extract was centrifuged (10 min, 10000 g). For use in T-cell proliferation assay, the supernatant was sterile filtered through a 0.2 -μm pore membrane and protein content was determined by the Bradford method (Bio-Rad protein assay) using BSA as standard. Aliquots were stored at –80° C. until use.

A.15. Sodium dodecylsulfate-polyacrylamide gel electrophoresis (SDS-PAGE) and Western blot.

SDS-PAGE was carried out in the discontinuous system described by Laemmli [1970]. Electrophoresis was run overnight under constant current (11 mA/gel). The gel was then washed for 1 h with 3 changes of 25 mM Tris, 192 mM glycine buffer pH 8.3. Proteins were transferred from the SDS slab gel to a nitrocellulose membrane (Hybond c) in the same buffer containing 20% (vol/vol) methanol, in an electrophoretic transfer chamber (Hoefer Scientific Instruments, San Francisco, Calif., USA) at 4° C. (2 h, 100 V). After transfer, the membrane was blocked by incubation with 1% BSA or 5% dried skimmed milk in washing buffer (2 h, RT). Conditions for incubation with anti-*T. gondii* antibody and labelled second antibody were as described for the immunoscreening. Anti-*T. gondii* human IgG were used at 10 μg/ml, anti-*T. gondii* mouse IgG at 5 μg/ml, and GAM-AP at a 1/10000 dilution. Protein molecular weight standards (myosin H-chain (200-kDa), phosphorylase b (97.4-kDa), bovine serum albumin (68-kDa), ovalbumin (43-kDa) carbonic anhydrase (29-kDa), β-lactoglobulin (18.4-kDa) and lysozyme (14.3-kDa) were obtained from BRL.

A.16. Preparation of antigen-bearing nitrocellulose particles

The preparation of nitrocellulose particles was carried out as previously described [Abou-Zeid et al., 1987]. After SDS-PAGE and electrotransfer, the nitrocellulose sheet was washed in phosphate-buffered saline for 30 min at RT. The position of molecular weight standards and the distribution of antigens were identified by Ponceau Red staining of vertical strips excised at the edges of the nitrocellulose sheet. The 60-mm-wide membrane containing the blotted material was divided in 3-mm-high horizontal strips. Positive and negative controls were prepared by dotting 25 μg of total soluble antigen onto a 20 mm$^2$ nitrocellulose circle. Each horizontal strip or three circles were transferred to a sterile tube, dissolved in 1 ml of dimethylsulfoxide (Merck, Darmstadt, Germany), and incubated for 1 h to ensure sterility of the samples. Antigen-bearing nitrocellulose particles were precipitated with an equal volume of carbonate-bicarbonate buffer (50 mM, pH 9.5) added dropwise with vigorous vortexing. The particles were washed two times with Hanks' Balanced Salt Solution (GIBCO) and finally resuspended in 1.5 ml of culture medium. They were stored at –20° C. until use. For proliferation assays, particles were used at a final dilution of 1/10.

A.17. Affinity purification of recombinant antigen-specific antibodies

Polyclonal antibodies specific for recombinant fusion protein were isolated from the IgG of the pool of human immune sera essentially as described by Prince at al. [1989]. A sample of lysogen lysate containing 1 mg total protein was electrophoresed in a 1.5×120-mm-section 7.5% polyacrylamide SDS-preparative gel and electrotransferred to nitrocellulose. After blocking, the membrane was incubated with anti-*T. gondii* human IgG (10 μg/ml in incubation buffer, overnight, 4° C.) and washed extensively. Vertical 3-mm-wide strips were cut on both edges of the nitrocellulose sheet and incubated sequentially with labelled second antibody and the chromogenic substrate in order to localize the reactive recombinant fusion protein. An horizontal strip containing this protein and bound antibodies was excised from the remaining central part of the nitrocellulose sheet and eluted in 0.2M glycine-HCl pH 2.5 for 15 min at RT. The eluate was neutralized by addition of a pretitrated volume of 2M Tris and diluted in incubation buffer containing 0.1% $NaN_3$.

A.18. Oligonucleotide synthesis and DNA sequencing

The oligonucleotides used as primers were synthesised by the phosphite-triester method in a Cyclone 8400 DNA synthesizer (New Brunswick Scientific Co., Edison, N.J., USA). Phage DNA was purified using Lambdasorb (Promega) according to the manufacturer's protocol and digested with EcoRI. The EcoRI insert of the recombinant phage was isolated by agarose gel electrophoresis, and subcloned into the EcoRI site of pBluescript KS+phagemid vector (Stratagene, La Jolla, Calif., USA) using standard techniques (Maniatis et al., 1982). Double-stranded plasmid DNA was sequenced by the chain termination method [Sanger et al., 1977] using T7 DNA polymerase (Pharmacia) and one of the following commercial primers: M13(−20) universal, M13 reverse, SK17-mer or KS17-mer (Stratagene), or synthesized internal primers.

EXAMPLE 1 a) Proliferative response of human PBMC to a soluble fraction of *T. gondii* (F3)

Tachyzoites of the RH strain of *T. gondii* were sonicated, centrifuged ($10^5$ g), and the soluble fraction (F3) used in a 5-day proliferation assay of PMBC from seropositive or seronegative individuals. In preliminary experiments, we found that lymphocytes from four seropositive donors were able to proliferate in response to the F3 while the lymphocytes of two seronegative individuals did not. The PBMC from all six donors responded to the polyclonal activator concanovalin A. Lymphocytes from a seropositive individual proliferated in a dose-dependent manner in the presence of F3, with the maximum response obtained with 25 $\mu$g/ml of antigen. No stimulation was observed in the case of a seronegative individual (SI<2 for all F3 concentrations tested).

As the tachyzoites used were obtained from the peritoneal cavity of mice, a check was made to ensure that the lymphocyte proliferation was not due to contaminating mouse proteins. To this end, peritoneal proteins and cells from non-infected control mice were obtained by injection of PBS in the peritoneal cavity. The recovered suspension was subjected to a cycle of sonication and centrifugation following the same protocol as for the F3 preparation (see Materials and Methods). The resulting preparation was tested in a proliferation assay using PBMC from a seropositive donor. The results indicated that the proliferation observed using the F3 is specific for *T. gondii* antigens since no response was observed when the extract of mice peritoneal proteins was used.

b) Generation of human T-cell clones specific for *T. gondii*

T-cell line was derived from the PBMC of a chronically infected donor by stimulation with F3 and was cloned by limiting dilution. A total of three cloning experiments was carried out. In the first two experiments, we used autologous irradiated PBMC+F3+IL-2 for stimulation of T-cell growth and obtained a total of 18 clones with a probability of monoclonality of 86% and 81%, respectively, as determined by the Poisson distribution. Five of the clones stopped to grow. In the third cloning experiment, we used allogeneic irradiated PBMC+PHA and IL-2. Five clones were recovered with a probability of monoclonality >90%.

c) Response of the T-cell clones to F3 and surface phenotype

The 18 clones obtained in the three cloning experiments were analyzed for their specificity to the antigen F3 in a proliferation assay and for expression of the cell surface markers CD4 and CD8. The results of the proliferation assay allowed us to classify the clones in three different groups. The first group consists of 12 clones specific for the antigen F3 and all belonging to the CD4 subset. The clones proliferated in the presence of the F3, but not in its absence or in the presence of proteins from peritoneal cavity of normal mouse (MPP). In this group, some clones responded strongly to the F3 (clones 32 and 29B), while others responded less well (clones 35 and 216).

In the second group, we classified two clones that responded weakly to the antigen as compared with the response of the clones of the first group, and one clone that did not respond (clone 34). Two of the clones belong to the CD4, and one to the CD8 subset. The low response to the F3 is due to an absence of IL-2 production since the addition of this lymphokine in the proliferation assay overcomes the unresponsiveness. The presence of IL-2 alone was either insufficient to induce proliferation (clones 27 and 215), or only able to induce weak proliferation (clone 34). Furthermore, the inability of these clones to produce IL-2 was confirmed (see below).

The third group contains three clones, the specificity of which towards *T. gondii* could not be demonstrated in the proliferation assay.

d) Production of IFN-$\gamma$ and IL-2

Because IFN-$\gamma$ and IL-2 have an important protection role in resistance against *Toxoplasma* infection, we tested the ability of the F3-specific T-cell clones to produce these lymphokines upon Ag stimulation. Detectable levels of IL-2 were found in the supernatants of five clones only, with clone 32 producing the highest lymphokine level (15 U/ml) No IL-2 activity was detected in the control supernatants, suggesting that the IL-2 was produced by the clones in response to the Ag. The production of IFN-$\gamma$ by the clones after stimulation with the antigen was also determined. The clones produced very heterogeneous levels of the lymphokine: some clones released insignificant amounts of IFN-$\gamma$ (<10 IU/ml; clones 215, 27, 21, 1G5, 2E3, 29B) as compared with baseline values (5 IU/ml produced by the APC alone). Clone 32 produced the highest amount of the lymphokine (1400 IU/ml) while the other clones produced intermediate levels (20–200 IU/ml) . When no antigen was added, no IFN-$\gamma$ was detected suggesting that IFN-$\gamma$ was produced in response to the antigen F3. Since some of the clones were not able to produce IL-2 upon stimulation or were unable to proliferate in the absence of exogenous IL-2, we also collected supernatants of the clones after stimulation with the antigen in the presence of exogenous IL-2 and quantified the IFN-$\gamma$ present. The presence of exogenous IL-2 enhanced the production of the IFN-$\gamma$ by most of the clones. Clones 32 and 27 did not show such enhancement. Some clones which failed to produce IFN-$\gamma$ in response to Ag alone, produced significant levels of IFN-$\gamma$ upon addition of IL-2 (clones 21, 29B, 2E3, 215).

e) Cross-reactivity of the T-cell clones

We investigated a possible *Toxoplasma* strain specificity of 7 T-cell clones by comparing their response to the RH strain with that observed using the also virulent Wiktor strain in a proliferation assay. The 7 clones, originally isolated with the RH strain, cross-reacted with the Wiktor strain.

In the cases of clones 216 and 29B, no appreciable difference was noted between the two strains but in cases of the 5 other clones (32, 2G8, 35, 2E3 and 31) a significantly lower response was observed against the Wiktor strain.

EXAMPLE 2 a) Response of T-cell clone 32 to different *T. gondii* strains

It has been found that the CD4+CD8- *T. gondii*-specific human T-cell clone 32 (TLC 32) defines an epitope common to the RH and Wiktor strains of *T. gondii*. However, these two strains are highly virulent to mice and do not form tissue cysts. In order to test the presence of the TLC 32-defined epitope in a strain more representative of isolates from naturally infected humans which are generally of low virulence to mice and cyst-forming, a soluble antigenic fraction (F3) was prepared from tachyzoites of the Gangji strain grown in cortisone-treated mice and tested in a proliferation assay. It was found that TLC 32 proliferated in response to antigen prepared from the three strains (RH, Wiktor, and Gangji) confirming that the TLC 32-defined epitope is conserved among *T. gondii* strains independently of their phenotype. A weaker response observed with the Gangji strain could be due to a lower relative concentration of the antigen in this strain.

b) Antigen recognition by T-cell clone 32 is HLA-DPw4-restricted

MHC restriction of TLC 32 reactivity was studied using MAbs directed to monomorphic determinants of class I and class II HLA gene products. As shown in Table I, the proliferative response of TLC 32 to the antigen in the presence of autologous B-LCL as APC was inhibited by anti-HLA-DP MAb (89% inhibition) and to a lesser extent by anti-HLA-DR MAb (51% inhibition). No inhibition was observed with the anti-HLA-DQ MAb, with an anti-HLA class I MAb, or with unrelated MAbs of the same subclass. The absence of inhibition of the PHA-induced T-cell proliferation by the MAbs excludes the possibility of an unspecific toxic effect of the antibody preparations. From these results, it can be concluded that antigen presentation to TLC 32 is DP-restricted; the partial inhibiti on observed with the anti-DR MAb could be due to a cross-reaction of this MAb with the DP molecules. The identification of the DP allele able to present antigen to TLC 32 was carried out using a panel of HLA-typed B-LCL as APC. The results shown in Table II clearly indicate that the antigen is recognized in association with DPw4.

EXAMPLE 3

Cloning, expression, and identification of the *T. gondii* antigen defined by T-cell clone 32

In order to identify the parasite antigen reactive with TLC 32, a *T. gondii* cDNA library was prepared in the cloning/expression vector λgt11 and individual recombinant antigens isolated from this library were tested for their reactivity with TLC 32. cDNA was synthesized from 5 μg poly(A)+ RNA purified from in vitro grown Wiktor strain tachyzoites and cloned in the λgt11 vector yielding a library of 4.9×10^5 independent phages, 87% of which were recombinants as determined by white/blue screening. Three hundred thousand phages of this library were plated and duplicate nitrocellulose membranes containing replicas of the plaques were screened either with a pool of immune human IgG or IgG of mice experimentally infected with the Wiktor *T. gondii* strain. One hundred and ninety-six plaques were immunodetected; among them, 62 produced antigens reactive with both anti-sera, 36 reacted only with human anti-serum, and 98 reacted only with the murine anti-serum. Three (Tg44 to Tg46), four (Tg40 to Tg43), and 37 (Tg1 to Tg32 and Tg34 to Tg38) recombinant phages reacting with mouse, human, or both antisera, respectively, were plaque-purified, and Y1089 lysogens corresponding to each of these recombinants were isolated. Western blot analysis of soluble extracts of induced cultures of these lysogens showed that all but three of them produced recombinant fusion proteins reactive with murine or human anti-*T. gondii* antiserum. The Mr of these fusion proteins were between 120±5-kDa and 190±5-kDa depending on the recombinant protein, indicating that the cloned cDNA had a coding capacity for a polypeptide with an approximate Mr between 5 and 65-kDa taking into account of Mr of 115-kDa for the β-galactosidase portion of the fusion protein. These fusion proteins were also recognized by a monoclonal antibody against β-galactosidase. Two recombinant clones (Tg7 and Tg17) expressed an antigen of unexpectedly low Mr (100-kDa and 57-kDa respectively) recognized by anti-*T. gondii* serum but not by anti-β-galactosidase antibody. Recombinant Tg45 did not express any immunologically detectable material. Crude lysates of the 44 recombinant lysogens were tested for their ability to induce proliferation of TLC 32. As shown in Table III, a significant proliferation of TLC 32 was observed in the presence of recombinant Tg34 lysogen lysate. Some proliferation was also observed in the presence of recombinant Tg28 lysate but its activity could not be reproduced in a separate experiment. λgt11 vector lysogen and the other recombinants did not display any stimulating activity on TLC 32. The response of TLC 32 to recombinant Tg34 is specific and dose-dependent. Moreover, the possibility that recombinant Tg34 could act as a nonspecific mitogen is excluded by the fact that it had no stimulatory activity on two other *T. gondii* specific TLC.

The reactivity of TLC 32 with the β-galactosidase fusion protein expressed in Tg34 lysogen was confirmed by the "T-cell blot" technique. Total lysate of the Tg34 or the λgt11 lysogen was fractionated by SDS-PAGE and transferred to nitrocellulose. Horizontal strips of the membrane were converted into antigen-bearing nitrocellulose particles and tested with TLC 32 in a proliferation assay. As expected, TLC 32 showed a peak of response with the fraction lo containing proteins of approximate Mr between 160 and 175-kDa and corresponding to the recombinant fusion protein Tg34. In addition, a strong proliferation was also observed with fractions containing antigens of 38 to 65-kDa, which could correspond to proteolytic degradation products of the recombinant antigen. No proliferation was observed with any of the fractions from the λgt11 vector lysogen.

EXAMPLE 4

Molecular mass of the *T. gondii* antigen encoded by clone Tg34

Antibodies specific for recombinant antigen Tg34 were isolated from anti-*T. gondii* human immune IgG by affinity on nitrocellulose blotted recombinant antigen. These monospecific antibodies were used to detect the corresponding *T. gondii* antigen on a Western-blot of total parasite lysate. Affinity-selected antibodies against recombinant Tg34 were found to react with a parasite antigen of Mr 54-kDa. Weak reaction was also observed with parasite components of Mr 59 and 66-kDa. The 54-kDa band was one of the major bands recognized by the original pool of human immune IgG. No reaction was observed with the control antibodies eluted from the blot of λgt11 vector lysogen. None of the antibodies reacted with the control blot of AGMK cells used to grow the parasite.

As a further confirmation of the Mr of the *T. gondii* antigen corresponding to recombinant Tg34, the antigenic component of *T. gondii* reacting with TLC 32 was directly identified by the "T-cell blot" technique. Nitrocellulose particles bearing size-fractionated antigens of *T. gondii* tachyzoites were tested in a proliferation assay with TLC 32. A major peak of proliferation with antigens of Mr 48–55-kDa was observed, tailing off in a higher Mr fraction (55–62-kDa). No proliferation was observed with any of the fractions from control uninfected AGMK cells. These results thus confirm those obtained with the Tg34-specific antibodies.

EXAMPLE 5

DNA sequence of clone Tg34 and deduced amino acid sequence

The EcoRI insert (±1800 bp) of recombinant Tg34 was subcloned into the EcoRI site of pBluescript KS +vector and characterized by digestion with several restriction enzymes. Unidirectional deletion clones were constructed and specific internal oligonucleotides were synthesized in order to obtain the full nucleotide sequence of the 1802 bp EcoRI fragment. This sequence contains a single long open reading frame of 1620 bp in frame with β-galactosidase. The sequence of the EcoRI linker used for cDNA cloning is found at the 5' end of the coding strand but not at the 3' end suggesting that the 3' end EcoRI site is probably an internal site of the *Toxoplasma* gene. The polypeptide encoded by this ORF has a calculated mass of 61.5-kDa fielding a β-galactosidase fusion protein of calculated mass 176.5-kDa, in agreement with the experimentally determined or (175±5-kDa). The first ATG codon is found at nucleotide position 574 and is not surrounded by sequences fulfilling the criteria for initiation of translation [Kozak, 1986]. The ATG initiation codon of the *Toxoplasma* gene is thus probably located upstream of the sequence present in the Tg34 cDNA clone. However, as mentioned above, this clone has a coding capacity for a polypeptide of Mr (61.5-kDa) larger than the corresponding mature *Toxoplasma* polypeptide (54-kDa). The missing amino-terminal residues thus probably belong to a pre/pro region. Indeed, lo analysis of the amino acid sequence by the methods of Eisenberg et al. [1984], Klein et al. [1985], and Rao and Argos [1986] based on amino acid hydrophobicity, predicts two membrane-associated regions (from residue 9 to 25 and from residue 464 to 485). The former region also displays significant homology with eukaryotic signal sequences suggesting a potential signal sequence cleavage site between residues 25 and 26 [von Heijne, 1986]. The classification of the second hydrophobic region as transmembranar [Eisenberg et al., 1984] suggests a possible membrane localization of the identified antigen. Finally, neither the DNA sequence nor the deduced amino acid sequence display any significant homology with the sequences of databanks (Genbank, release 61.0; PIR, release 21.0) or the seven *T. gondii* genes or gene fragments already reported [Burg et al., 1988; Nagel and Boothroyd, 1988; Burg et al., 1989; Cesbron-Delauw et al., 1989; Johnson et al., 1989; Prince et al., 1989].

EXAMPLE 6

Expression in *E. coli* using the pIGAL12 vector

All standard techniques were performed as described in Maniatis et al. (1982). Vector: Five µg of purified DNA from plasmid pIGAL12 (Saman et al., 1990) was digested with 30 units EcoRI in a total volume of 20 µl for 4 h at 37° C. One l (24 units) of calf intestine alkaline phosphatase (CIAP) was then added and the reaction was allowed to proceed for 30 min at 37° C. After a further addition of 1 µl (24 units of CIAP and incubation at 37° C. for 30 min, the reaction mixture was incubated at 65° C. for 10 min, extracted twice with phenol-chloroform-isoamylalcohol (25:24:1,v:v:v), twice with diethylether, after which the DNA was ethanol-precipitated in the presence of 2.5M ammonium acetate (overnight, 4° C.). The DNA was collected by centrifugation, the pellet was rinsed with 70% ethanol in water, recovered by centrifugation, dried and resuspended in 25 µl of TE buffer (10 mM Tris-HCl, 1 mM EDTA, pH 8).

Insert: Five µg of purified DNA from plasmid pBluescriptKS+-Tg34 (plasmid resulting from the insertion of the Tg34 cDNA clone in the EcoRI site of pBluescriptKS+ as described in A.18 supra) was digested with 30 units EcoRI in a total volume of 50 µl for 3 h at 37° C. The reaction mixture was incubated at 65° C. for 10 min and loaded on a 1.4% agarose gel. After electrophoresis, the DNA fragment with a length of approximately 1800 bp was extracted from the agarose, purified by two extractions with phenol-chloroform-isoamylalcool, two extractions with diethylether, and adsorption on silica matrix (Geneclean, BIO 101 Inc., La Jolla, Calif.) according to the manufacturer's instructions. The DNA was finally recovered in 20µl of $H_2O$ and quantified by agarose gel electrophoresis, ethidium bromide-staining, and comparison with a standard DNA preparation.

pIGAL12Tg34: One hundred and fifty ng of vector and 50 ng of insert were incubated in the presence of 1 unit T4 DNA ligase in a final volume of 15 µl of ligation buffer (50 mM Tris-HCl, 10 mM $MgCl_2$, 1 mM dithiothreitol, 1 mM adenosine triphosphate, pH 7.5) overnight at 14° C. After incubation at 65° C. for 10 min, 5 µl of reaction mix was used to transform 100 µl of competent cells from *E. coli* strain DH1 (ATCC 33849) lysogen for phage lambda. Preparation of competent cells and transformation was performed as described by Maniatis et al. (1982). Cells were plated on ampicillin-containing selection medium and grown at 37° C. Plasmid DNA was prepared and analyzed by agarose gel electrophoresis after digestion with restriction enzymes as described by Maniatis et al. (1982).

Induction of recombinant fusion protein expression: *E. coli* MC1061 (ATCC 53338) carrying the plasmid pCI857 (Remaut et al., 1981) cells were made competent and transformed with plasmid pIGAL12Tg34 or the control plasmid pIGAL12 as described by Maniatis et al. (1982). Cells were plated on ampicillin-containing selection medium and grown at 28° C. An overnight culture at 28° C. of one of the transformants in LB medium (Maniatis et al., 1982) containing 50 µg/ml ampicillin was used to inoculate a fresh culture in the same medium. The culture was incubated at 28° C. with vigorous shaking until the optical density, measured at 590 nm, reached a value of 0.2 (1-cm long optical path). The temperature of the culture was then rapidly raised to 42° C. with vigorous shaking. Samples were drawn at various time intervals. Cells were rapidly collected by centrifugation (12000 g, 30 s) and resuspended in SDS-sample buffer (62 mM Tris-HCl, 5% mercaptoethanol, 10% glycerol, 2.5% SDS, 0.005% bromophenol blue, pH 6.8). Samples were incubated for 5 min in a boiling water bath, chilled and kept frozen at −20° C. until analysis by SDS-PAGE and western blot.

Expression of clone Tg34 in *E. coli* using the pIGAL12 vector

The EcoRI insert of recombinant Tg34 was inserted in the EcoRI site of the expression vector pIGAL12. Clones containing the insert in the correct orientation with respect to expression were selected according to the results of restriction enzyme analysis with BamHI and BqlI. The resulting recombinant plasmid (pIGAL12Tg34) encodes a fusion polypeptide consisting of 49 amino acid encoded by the plasmid vector at its amino-terminus and the amino acid sequence encoded by clone Tg34 and displayed in FIG. 2 at its carboxy-terminus. The expression of this fusion polypeptide is under the control of the $P_R$ promoter of phage lambda. When *E. coli* strain MC1061 carrying both plasmid pIGAL12Tg34 and plasmid pCI857 that codes for a thermosensitive repressor of phage lambda $P_R$ promoter were incubated at 42° C., the repressor was inactivated, and expression of the fusion polypeptide occurred. Samples of the bacterial culture taken at several time intervals (1 to 5 hours) after shifting the temperature to 42° C. were analyzed by SDS-gel electrophoresis, Western blot and immunodetection with a pool of sera of *Toxoplasma*-infected individuals. A major immunoreactive protein with an apparent molecular mass of 77-kDa was observed in samples of bacteria carrying the recombinant plasmid pIGAL12Tg34 but not in bacteria carrying the vector pIGAL12. Other immunologically reactive bands of lower molecular mass (70 to 43-kDa) were also observed in extracts of bacteria carrying pIGAL12Tg34; they probably correspond to proteolytic degradation products of the recombinant fusion polypeptide. Expression of the fusion polypeptide could also be detected by Western blot using a monoclonal antibody directed to an epitope present on the amino acid sequence of the fusion polypeptide encoded by the expression vector pIGAL12. These results indicate that the coding information of clone Tg34 can be expression in *E. coli* and that the resulting recombinant fusion protein is reactive with sera of *Toxoplasma*-infected individuals.

TABLE I

Blocking of proliferative response of T-cell clone 32 by anti-HLA class II monoclonal antibodies.
[$^3$H] thymidine incorporation (cpm)

| MAb | F3 | PHA |
|---|---|---|
| None | 19038 ± 1982 | 25671 ± 1246 |
| anti-DR | 9480 ± 3146 (51) | 27367 ± 383 (−6) |
| anti-DP | 2240 ± 116 (89) | 24148 ± 3482 (6) |
| anti-DQ | 18895 ± 4410 (0) | 26251 ± 380 (−2) |

T cells (2 × 10$^4$/well) were stimulated with F3 (3 μg/ml) or PHA (1%, v:v) in the presence of cryopreserved autologous irradiated B-LCL (2 × 10$^4$/well). Anti-MHC Class II Mabs were added at a final concentration of 3.1 μg/ml. Proliferation was assessed three days later by [$^3$H] thymidine incorporation. Results are mean ± SD of triplicates. Percentage of inhibition relative to the control without MAb is indicated in parentheses.

TABLE II

HLA-DP restriction of T-cell clone 32
[$^3$H] thymidine incorporation (cpm)

| B-LCL (APC) | DPw | F3 | — |
|---|---|---|---|
| Autologous | ND$^a$ | 16854 ± 487 | 1002 ± 489 |
| DOC3 | 1, 4 | 8961 ± 303 | 907 ± 148 |
| JAH | 3, 4 | 9914 ± 642 | 1042 ± 348 |
| MS7 | 4, 5 | 16541 ± 669 | 1279 ± 158 |
| P5493 | 1, 3 | 1202 ± 138 | 1757 ± 132 |
| RAG | 2, 4 | 13239 ± 815 | 677 ± 104 |
| HID | 2, 5 | 953 ± 50 | 757 ± 210 |
| J1066 | 1, 5 | 1151 ± 232 | 1530 ± 250 |
| J929 | 4, 6 | 19396 ± 231 | 2816 ± 69 |

T cells (2 × 10$^4$/well) were incubated with or without F3 (10 μg/ml) in the presence of cryopreserved irradiated B-LCL (2 × 10$^4$/well), either autologous or from a panel of HLA-typed cells. Proliferation was assessed as described in Table I. Results are mean ± SD of triplicates. Values corresponding to significant proliferation are underlined.
ND$^a$: not determined.

TABLE III

Proliferation of T-cell clone 32 in response to recombinant *T. gondii* antigens expressed in *E. coli*
Protein concentration (μg/ml)

| Lysate | 0.03 | 0.3 | 3 |
|---|---|---|---|
| λgt11 | 2380 ± 1215 | 1400 ± 521 | 915 ± 216 |
| Tg34 | 1175 ± 277 | 1065 ± 269 | 11725 ± 65 |
| Tg28 | 4288 ± 543 | 2490 ± 2556 | 4977 ± 2696 |
| All others | ≦2250 | ≦1722 | ≦1991 |
| *T. gondii* F3 (30 μg/ml): | | 31742 ± 2297 | |
| None | | 818 ± 37 | |

T cells (2 × 10$^4$/well) were incubated with serial dilutions of lysogen crude lysates or *T. gondii* F3 in the presence of autologous irradiated B-LCL (5 × 10$^4$/well). Proliferation was assessed as described in Table I. Results are expressed in cpm and are the means ± SD of triplicates.

References

Abou-Zeid, C., Filley, E., Steele, J. and Rook, G. A. W. (1987) *J. Immunol. Method* 98, 5–10.

Beverley, J. K. A. (1976) *Vet. Rec.* 99, 123–127.

Beverley, J. K. A., Archer, J. F., Watson, W. A. and Fawcett, A. R. (1971) *Br. Vet. J.*, 127, 529 Burg, J. L., Perelman, D., Kasper, L. H., Ware, P. L. and Boothroyd, J. C. (1988) *J. Immunol.* 141, 3584–3591.

Burg, J. L., Grover, C. M., Pouletty, P. and Boothroyd, J. C. (1989) *J. Clin. Microbiol.* 27, 1787–1792.

Cesbron-Delauw, M. F., Guy, B., Torpier, G., Pierce, R. J., Lenzen, G., Cesbron, J. Y., Charif, H., Lepage, P., Darcy, F., Lecocq, J. P. and Capron, A. (1989) *Proc. Natl. Acad. Sci. USA* 86, 7537–7541.

De Meuter, F., Fameree, L. and Cotteleer, C. (1975) *Protistologica* XI, 499–507.

Eisenberg, D., Schwarz, E., Komaromy, M. and Wall, R. (1984) *J. Mol. Biol.* 179, 125–142.

Francois, J., Jadin, J., Wery, M. and Van De Casteele, J. (1963) *Bull. Acad. Rov. Med. Bel.* III, 459–485.

Frenkel, J. K. (1967) *J. Immunol.* 98, 1309–1319.

Frenkel, J. K. and Escajadillo, A. (1987) *Am J. Trop. Med. Hyg.* 36, 517.

Gubler, U. and Hoffman, B. J. (1983) Gene 25, 263–269.

Hughes, H. P. A. (1985) *Curr. Top. Microbiol. Immunol.* 120, 105–139.

Hughes, H. P. A., Connelly, C. A., Strangeways, J. E. M., and Hudson, L. (1984) *Clin. Exp. Immunol.* 58, 539–547.

Huynh, T. V., Young, R. A. and Davis, R. W. (1985) In *DNA cloning*, ed. Glover, D. M. (IRL press, Oxford), Vol. 1, pp. 49–78.

Johnson, A. M., McDonald, P. J. and Illana, S. (1986) *Mol. Biochem. Parasitol.* 18, 313–320.

Johnson, A. M., Illana, S., McDonald, P. J. and Takashi, A. (1989) *Gene* 85, 215–220.

Klein, P., Kanehisa, M., and Delisi, C. (1985) *Biochim. Biophys. Acta* 815, 468–476.

Kozak, M. (1986) *Cell* 44, 283–292.

Laemmli, U. K. (1970) *Nature* 227, 680–685.

Lamb, J. R. and Young, D. B. (1987) *Immunology* 60, 1–5.

Lelong, M. and Desmonts, G. (1951) *C. R. Soc. Biol.* 145, 1660–1661.

Maniatis, T., Fritsch, E. F. and Sambrook, J. (1982) *Molecular Cloning* (Cold Spring Harbor Laboratory, Cold Spring Harbor, N.Y.).

McCabe, R. and Remington, J. S. (1988) *N. Engl. J. Med.* 318, 313–315.

Mustafa, A. S., Gill, H. K., Nerland, A., Britton, W. J., Mehra, V., Bloom, B. R., Young, R. A. and Godal, T. (1986) *Nature* 319, 63–66.

Mustafa, A. S., Oftung, F., Deggerdal, A., Gill, H. K., Young, R. A. and Godal, T. (1988) *J. Immunol.* 141, 2729–2733.

Nagel, S. D. and Boothroyd, J. C. (1988) *Mol. Biochem. Parasitol.* 29, 261–273.

Nathan, C. F., Prendergast, F. J., Wiebe, M. E., Stanley, E. R., Platze, E., Remold, H. G., Welte, K., Rubin, B. Y. and Murray, H. W. (1984) *J. Exp. Med.* 160, 600–605.

Pfefferkorn, E. R. (1984) *Proc. Natl. Acad,. Sci USA* 81, 908–912.

Pfefferkorn, E. R. and Pfefferkorn, L. C. (1976) *Exp. Parasitol* 39, 365.

Prince, J. B., Araujo, F. G., Remington J. S., Burg, J. L., Boothroyd, J. C. and Sharma, S. D. (1989) *Mol. Biochem. Parasitol.* 34, 3–14.

Rao, M. J. K. and Argos, P. (1986) *Biochim. Biophys. Acta* 869, 197–214.

Remaut, E., Stanssens, P., and Fiers, W. (1981) *Gene:* 15, 35 81–93.

Remington, J. S., Miller, M. J. and Brownlee, I. (1968) *Pediatrics* 41, 1082–1091.

Remington, J. S. and Krahenbuhl, J. L. (1982) in *Immunology of human infection,* eds. Nahmias, A. J. and O'Reilly, R. J. (Plenum Publishing, New York), Part II, pp. 327–371.

Roder, J. C., Cole, S. P. C., Kozbor, D. (1896) in *Methods in Enzymology,* 121 eds Langone, J. L., Vunakis, H. V. (Academic Press, London), pages 145–146.

Sabin, A. B. (1941) *J. Am. Med. Assoc.* 116, 801–807.

Saman, E., Breugelmans, K., Heyndrickx, L., and Merregaert, J. (1990) *J. Virol.* 64, 6319–6324.

Sanger, F., Nicklen, S. and Coulson, A. R. (1977) *Proc. Natl. Acad. Sci. USA* 74, 5463–5467.

Sethi, K. K. Omata, Y. and Brandis, H. (1985) *Immunobiology* 170, 270–283.

Suzuki, Y., Conley, F. K. and Remington, J. S. (1989) *J. Immunol.* 143, 2045–2050.

Suzuki, Y., Orellana, M. A., Schreiber, R. D. and Remington, J. S. (1988) *Science* 240, 516–518.

Suzuki, Y. and Remington, J. S. (1988) *J. Immunol.* 140, 3943–3946.

Suzuki, Y. and Remington, J. S. (1990) *J. Immunol.* 144, 1954–1956.

von Heijne, G. (1986) *Nucleic Acids Res.* 14, 4683–4690.

Waldeland, H. and Frenkel J. K. (1983) *J. Parasitol.* 69, 60.

Waldeland, H. Pfefferkorn, E. R. and Frenkel, J. K. (1983) *J. Parasitol.* 69, 171.

---

What is claimed is:

1. A isolated DNA fragment which is selected from the group consisting of:

(a) a DNA sequence encoding the amino acid sequence represented by the sequence shown in SEQ ID No:1;

(b) a DNA sequence which is degenerate as a result of the genetic code to the DNA sequence (a) above; and (c) a DNA sequence which hybridizes under stringent conditions to the complementary sequence of the DNA sequences (a) or (b) above; said isolated DNA fragment encoding a protein of about 54 kDa in molecular weight (determined by Western blotting) which induces proliferation of a *Toxoplasma gondii* specific human T-cell clone, and is (i) capable of being recognized by and binds to antibodies in sera or other biological samples of *T. gondii* chronically infected humans or animals; or (ii) capable of raising and raises antibodies following internal administration to a human or an animal.

2. An isolated DNA fragment comprising the complementary sequence of the DNA fragment claimed in claim 1.

3. A vector comprising a DNA according to claim 1.

4. A vector comprising a DNA according to claim 2.

5. A vector as claimed in claim 3 which encodes an antigen of *T. gondii* about 54-kDa in molecular weight as determined by Western blotting.

6. A host cell transformed with the vector of claim 3.

7. A host cell transformed with the vector of claim 5.

8. A method for producing a *T. gondii* antigen comprising incubating a host cell according to claim 6 in a culture medium under conditions which allow the expression of said antigen; and recovering the antigen therefrom.

9. A method for producing a *T. gondii* antigen comprising incubating a host cell according to claim 7 in a culture medium under conditions which allow the expression of said antigen; and recovering the antigen therefrom.

10. The isolated DNA fragment of claim 1 wherein the protein comprises the entire amino acid sequence shown in Sequence ID No. 1.

11. The vector of claim 3 which is selected from the group consisting of plasmid, bacteriophage, cosmid, and recombinant virus.

12. The vector of claim 4 which is selected from the group consisting of plasmid, bacteriophage, cosmid, and recombinant virus.

13. The host cell of claim 6 which is selected from the group consisting of bacterial, mammal, insect, and yeast.

14. The host cell of claim 13 which is *Escheria coli*.

15. The host cell of claim 7 which is selected from the group consisting of bacterial, mammal, insect, and yeast.

16. The host cell of claim 15 which is *Escheria coli*.

17. An isolated recombinant DNA fragment which encodes at least the corresponding portion of an Mr of at least 5 kDa of a 54 kDa protein which is diagnostic of chronic infections of *T. gondii* determined on a lysate of *T. gondii* in its tachyzolte life cycle, has the corresponding portion of the amino acid sequence of SEQ. ID No:1, s immunogenic, is recognized by antibodies in the sera or other biological samples of chronic infections of *T. gondii* in humans or animals, induces the proliferation of a *Toxoplasma gondii* (*T. gondii*) specific human T-cell clone, binds to immune human and mouse sera, has an epitope defined by the T-cell clone which is conserved amongst different strains of *T. gondii* independently of their phenotype, produces IFN-γ and elicits a cell-mediated immune response.

18. The isolated DNA sequence of claim 1 which encodes for the antigen, which is a recombinant sequence.

* * * * *